United States Patent [19]

Crook et al.

[11] Patent Number: 4,699,131
[45] Date of Patent: Oct. 13, 1987

[54] OPHTHALMIC SURGICAL DRAPE SUPPORT

[76] Inventors: John A. Crook, Box 341 1025 Fieldown Street, Cumberland, Ontario, Canada, K0A1S0; Garth A. Taylor, 510-520 Second Street East, Cornwall, Ontario, Canada, K0A1Z6

[21] Appl. No.: 836,058

[22] Filed: Mar. 4, 1986

[30] Foreign Application Priority Data

Mar. 14, 1985 [CA] Canada .................................. 476465

[51] Int. Cl.⁴ ...................... A61M 16/01; A61F 15/00
[52] U.S. Cl. ............................ 128/132 D; 128/206.28; 128/200.24
[58] Field of Search ............... 128/132 R, 128 D, 163, 128/200.24, 206.28, 206.21; 248/165, 166, 188.2, 188.6, 170, 168; 604/304; 5/440

[56] References Cited

U.S. PATENT DOCUMENTS

| | | | |
|---|---|---|---|
| 1,711,585 | 5/1929 | Brunhoff | 248/166 |
| 2,940,708 | 6/1960 | Grimal | 248/168 |
| 3,347,544 | 10/1967 | Uffenorde | 128/200.24 X |
| 3,403,677 | 10/1968 | Strove | 128/132 D X |
| 3,464,411 | 9/1969 | Martinez | 128/200.24 X |
| 3,859,993 | 1/1975 | Bitner | 128/200.24 X |
| 4,122,848 | 10/1978 | Carpel | 128/132 D |
| 4,465,066 | 8/1984 | Carpel | 128/132 D |

Primary Examiner—Robert A. Hafer
Assistant Examiner—Kathleen J. D'Arrigo

[57] ABSTRACT

A surgical drape support for use in eye surgery or other surgery, for maintaining adjustable support of surgical drapes above the patient's nose and mouth, creating a small tent into which oxygen is supplied by a hose, allowing the patient to breathe freely. With the front legs of the support placed between the patient's shoulders and the operating table the greatest stability is achieved and the rear legs find their best location as the support is adjustably positioned for height by raising or lowering the frame on its legs with the locking screws just loose enough for a pivoting motion. The knurled locking screws are tightened to maintain the prefixed position and four point stability of the instrument on the operating table, resulting in a more relaxed state of mind for both patient and surgeon.

8 Claims, 4 Drawing Figures

OPHTHALMIC SURGICAL DRAPE SUPPORT

This invention relates to a manually operable instrument for supporting and positioning sterile surgical drapes comfortably above a patient's face during eye surgery or other facial surgery where a local anesthesia is used.

During surgery, especially eye surgery where a local anesthesia is employed to accomplish the surgical techniques, the patient is awake and the surgical drapes cover the entire face except for the eye which is being operated on. It is a recognized problem that some patients move their heads during surgery to find a better position, because sheets, hoses or other devices are resting on their face. Some patients feel claustrophobic and apprehensive about having their heads covered while under local anesthesia and in having surgery where unfamiliar devices are attached to them such as oxygen hoses, surgical drapes or supports that have bothersome facial contact. The risk of mishap with sharp instruments used by the surgeon making precise incisions by microscope is a concern and the patient must be kept comfortable to minimize the chances of this happening. The advantages of using a local anesthesia is especially obvious in the case of older patients when the recovery from mild local freezing is compared against the stronger drugs used in heavier doses to achieve a general anesthesia. It is this desire to minimize risk to the patient that surgical drape supports are employed.

The prior art devices have usually been attached to the patient's face which could be bothersome, and in other instances cause allergic reaction to the adhesives used. For example see U.S. Pat. No. 4,465,066 issued to Carpel Aug. 14, 1984 which shows a cardboard drape support with adhesive discs for attachment to the patient's face. U.S. Pat. No. 4,122,848 issued to Carpel Oct. 31, 1978 also shows a device which rests on the patient's nose and is secured in place with adhesive tape.

Other prior art devices have been bulky support structures or cumbersome devices which are not readily adjustable as shown in U.S. Pat. No. 3,347,544 issued to Uffenorde in Oct. 17, 1967 and on Oct. 1, 1968 U.S. Pat. No. 3,403,677 issued to Struve.

The present invention overcomes the disadvantages of the prior art devices by providing a surgical drape support which is adjustable by the surgeon to fit all patients in such a way so as to be comfortable to both patient and surgeon in that it does not bother the patient by touching them on the face, and is positioned out of the way of interference to the doctor. The instrument is compact when collapsed and can easily be autoclaved with other instruments for sterilization. Use of this support instrument requires no special operating table equipment.

It has further been found that previous disadvantages have been overcome by providing four legs adjustably and pivotally connected to the support frame to offer maximum instrument stability on the operating table by itself without touching the patient's face and securely support the surgical drapes and oxygen hose away from the patient's nose and mouth in such a way as to be acceptable to the surgeon's space requirements.

In drawings which illustrate by way of example, a particular embodiment of the present invention:

Figure 1:
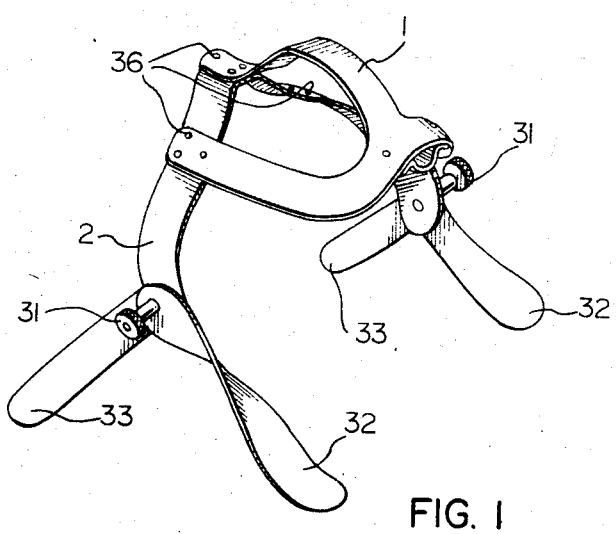
FIG. 1 is a perspective view of this embodiment.
Figure 2:
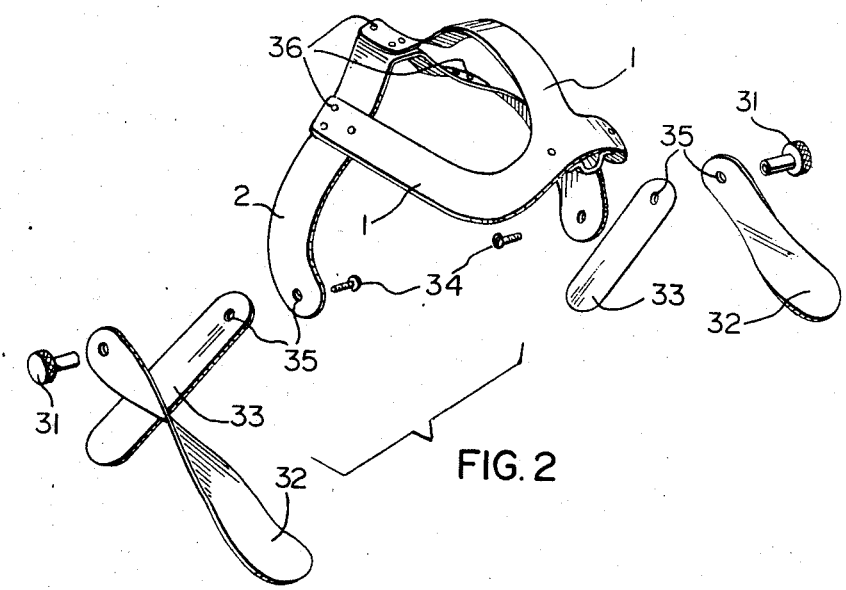
FIG. 2 is a perspective view of this embodiment disassembled.
Figure 3:
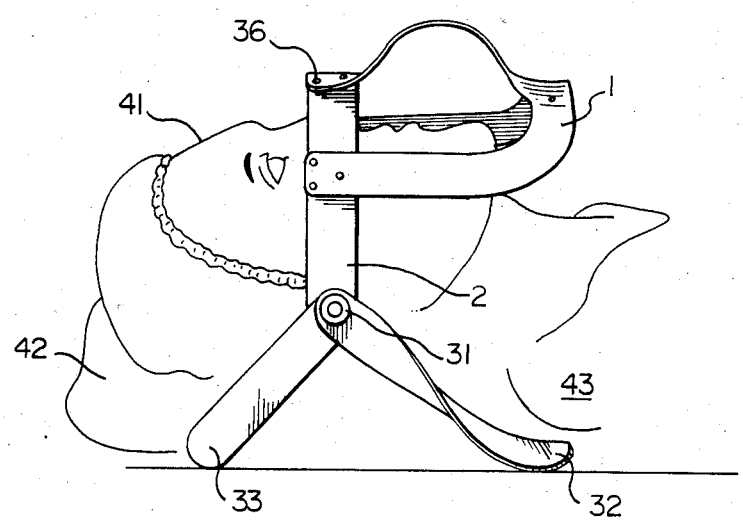
FIG. 3 is an illustration of the surgical drape support in position over a patient's head when viewed from the side.
Figure 4:
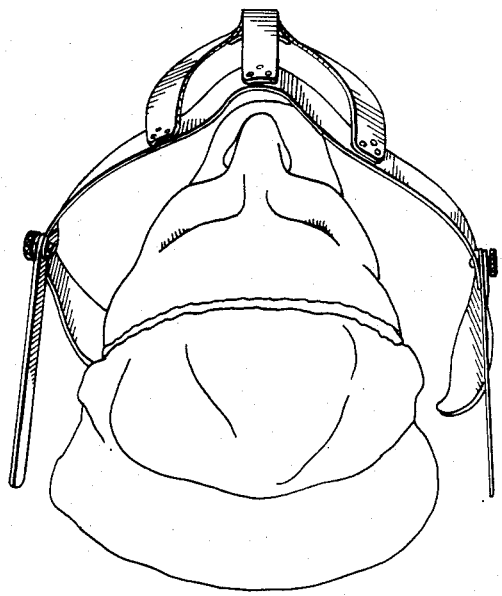
FIG. 4 illustrates the surgical drape support in use over a patient's head when viewed from the end of the operating table.

The instrument illustrated in FIG. 1 comprises of a support frame consisting of a U-shaped member 2 and a W-shaped member 1 permanently held together by rivets 36 at the junction where the arms of the W-shaped member centrally meet the U-shaped member 2. Front legs 32 and rear legs 33 are paired in left and right sets because the ¼ twist in the front legs is 90 degrees clockwise for the right side and 90 degrees counter clockwise for the left side in order to accomodate the anatomy of the patient's neck and shoulders when the instrument is in use. Machine screws 34 as shown in FIG. 2 are permanently threaded in holes 35 of support frame arms 2. Left and right leg pairs are attached respectively to either side of support frame arms by placing screw 34 through holes 35 in legs 32 and 33. Knurled knobs 31 are screwed onto axle formed by screws 34 and tension is adjusted by turning knobs 31 on both sides simultaneously to clamp the legs to frame arms when the desired position of the support frame is obtained. FIG. 3 shows an embodiment of this invention in a prefixed position over a patient's head prior to oxygen hose and surgical drape placement, and further shows how the patient's shoulder 43 stabilizes the front legs 32 against the table. FIG. 4 in operation identical to FIG. 3 illustrates the instrument when viewed from the head end of the operating table. While not illustrated it will be clear to one skilled in the art that an appropriate connection means may be provided on the instrument to secure the oxygen supply.

Having thus described the invention the embodiments in which an exclusive property or privilege is claimed are defined as follows:

1. A surgical instrument for supporting a surgical drape over a patient's nose and mouth while the patient is on an operating table comprising:
   a. a support frame curved to acomodate the anatomy of the face and support surgical drapes away from the mouth and nose providing a tent like area acceptable to the surgeon's space requirements, wherein the support frame comprises a U-shaped member adapted to arch across the patient's face above the nose, from ear to ear, and a W-shaped member affixed centrally to and extending downwardly from the U-shaped member adapted to extend over the patient's mouth and chin.
   b. pairs of front and back legs adjustably attached to the sides of the support frame to provide stable four point contact of the instrument with the operating table, the front contoured to the patient's neck and shoulder anatomy and disigned in use to rest under the patient's shoulders and on the table to thereby hold and stabilize the instrument in proper position,
   c. an adjustable means associated with the legs and frame to permit raising and lowering the height of the instrument and tilting the support frame forwards or backwards and clamping of the instrument in the desired prefixed position.

2. A surgical instrument according to claim 1 wherein the frame is constructed of material that is manually reshapeable thereby allowing the frame to be reshaped by hand compression or expansion to adjust the width of the support from ear to ear.

3. A surgical instrument according to claim 2 wherein the material of the support is metal, 4. A surgical instrument according to claim 3 wherein the metal is tempered aircraft aluminum.

5. A surgical instrument according to claim 3 wherein the middle arm of the W-shaped member is convexly contoured to provide a tenting space for the oxygen when the instrument is covered with surgical drapes, 6. A surgical instrument according to claim 1 wherein the support frame comprises a bracket attached to the W-shaped member to attach and hold an oxygen supply hose toward the mouth and nose of the patient, 7. A surgical instrument according to claim 1 wherein the legs are pivotally secured to the ends of the U-shaped member, 8. A surgical instrument according to claim 7 wherein the legs are adjustably attached to the U-shaped member by means of knurled knobs,

* * * * *